US006989021B2

(12) United States Patent
Bosma et al.

(10) Patent No.: US 6,989,021 B2
(45) Date of Patent: Jan. 24, 2006

(54) RETRIEVABLE MEDICAL FILTER (75) Inventors: Gjalt Bosma, Opeinde (NL); Hendrik G. Breedveld, Meppel (NL); Thomas W. Huitema, Cincinnati, OH (US); Rudolf T. Mulder, Groningen (NL); James H. Silver, Redwood City, CA (US)

(73) Assignee: Cordis Corporation, Miami Lakes, FL (US)

( * ) Notice: Subject to any disclaimer, the term of this patent is extended or adjusted under 35 U.S.C. 154(b) by 367 days.

(21) Appl. No.: 10/403,470

(22) Filed: Mar. 31, 2003

(65) Prior Publication Data

US 2004/0088001 A1 May 6, 2004

Related U.S. Application Data

(63) Continuation-in-part of application No. 10/285,218, filed on Oct. 31, 2002.

(51) Int. Cl.
*A61M 29/00* (2006.01)

(52) U.S. Cl. ..................................... 606/200
(58) Field of Classification Search ............... 606/200, 606/159
See application file for complete search history.

(56) References Cited

U.S. PATENT DOCUMENTS

| | | | |
|---|---|---|---|
| 4,425,908 A | 1/1984 | Simon | |
| 4,494,531 A | 1/1985 | Gianturco | |
| 4,662,885 A | 5/1987 | DiPisa, Jr. | |
| 4,793,348 A | 12/1988 | Palmaz | |
| 4,832,055 A | 5/1989 | Palestrant | |
| 4,873,978 A | 10/1989 | Ginsburg | |
| 4,943,297 A | 7/1990 | Saveliev et al. | |
| 4,957,501 A | 9/1990 | Lahille et al. | |
| 4,969,891 A | 11/1990 | Gewertz | |
| 4,990,156 A | 2/1991 | Lefebvre | |
| 5,108,418 A * | 4/1992 | Lefebvre | ............. 606/200 |
| 5,133,733 A | 7/1992 | Rasmussen et al. | |
| 5,147,379 A | 9/1992 | Sabbaghian et al. | |
| 5,188,616 A | 2/1993 | Nadal | |
| 5,234,458 A | 8/1993 | Metais | |
| 5,242,462 A | 9/1993 | El-Nounou et al. | |
| 5,300,086 A | 4/1994 | Gory et al. | |
| 5,329,942 A | 7/1994 | Gunther et al. | |
| 5,350,398 A | 9/1994 | Pavcnik et al. | |
| 5,370,657 A | 12/1994 | Irie | |
| 5,397,310 A | 3/1995 | Chu et al. | |
| 5,413,586 A | 5/1995 | Dibie et al. | |
| 5,415,630 A | 5/1995 | Gory et al. | |
| 5,531,788 A | 7/1996 | Dibie et al. | |
| 5,601,595 A | 2/1997 | Smith | |

(Continued)

FOREIGN PATENT DOCUMENTS

DE      40 30 998 A1     4/1991

(Continued)

*Primary Examiner*—Anhtuan T. Nguyen
*Assistant Examiner*—Elizabeth Houston
(74) *Attorney, Agent, or Firm*—Michael W. Montgomery (57) ABSTRACT

The present invention relates to a retrievable medical filter which can be placed in a blood vessel or other body passage. The filter has improved structural features for enhancing its performance, including deployment, filtration and position stability at the desired site, as well as retrievability. The filter may preferably have a hook structure that provides multiple retrieval surfaces, or may be provided with anchors for removably retaining the filter in position. A filter may be designed with one end being customized for retrieval and the other end being customized for position retention, in which case a cartridge may be provided to ensure proper orientation of the filter during delivery.

7 Claims, 12 Drawing Sheets

| U.S. PATENT DOCUMENTS | | | |
|---|---|---|---|
| 5,626,605 A | 5/1997 | Irie et al. | |
| 5,634,942 A | 6/1997 | Chevillon et al. | |
| 5,669,933 A | 9/1997 | Simon et al. | |
| 5,683,411 A | 11/1997 | Kavteladze et al. | |
| 5,695,518 A | 12/1997 | Laerum | |
| 5,709,704 A | 1/1998 | Nott et al. | |
| 5,720,764 A | 2/1998 | Naderlinger | |
| 5,746,767 A | 5/1998 | Smith | |
| 5,800,457 A | 9/1998 | Gelbfish | |
| 5,836,969 A * | 11/1998 | Kim et al. | 606/200 |
| 5,853,420 A | 12/1998 | Chevillon et al. | |
| 6,077,274 A | 6/2000 | Ouchi et al. | |
| 6,245,012 B1 * | 6/2001 | Kleshinski | 623/1.11 |
| 6,277,139 B1 | 8/2001 | Levinson et al. | |
| 2002/0111647 A1 * | 8/2002 | Khairkhahan et al. | 606/200 |
| 2003/0065354 A1 * | 4/2003 | Boyle et al. | 606/200 |
| 2003/0130680 A1 * | 7/2003 | Russell | 606/200 |

| FOREIGN PATENT DOCUMENTS | | | |
|---|---|---|---|
| DE | 195 09 464 C1 | | 3/1995 |
| EP | 0 462 008 A1 | | 12/1991 |
| EP | 0 815 803 A1 | | 1/1998 |
| EP | 0 968 688 A1 | | 5/2000 |
| EP | 1 138 277 A1 | | 10/2001 |
| EP | 1 258 228 A1 | | 11/2002 |
| FR | 2 606 642 A1 | | 5/1988 |
| FR | 2 718 950 A1 | | 10/1995 |
| WO | 95/09567 | | 4/1995 |
| WO | 96/17634 | | 6/1996 |
| WO | 98/02112 | | 1/1998 |
| WO | WO 99/25252 | * | 5/1999 |
| WO | WO 00/67669 | | 5/2000 |
| WO | WO 00/67669 | * | 8/2000 |

* cited by examiner

RETRIEVABLE MEDICAL FILTER

CROSS-REFERENCE TO RELATED APPLICATION

The present application is a continuation-in-part of Ser. No. 10/285,218, entitled "Vascular Filter with Improved Anchor or Other Position Retention," filed Oct. 31, 2002.

BACKGROUND AND SUMMARY OF THE INVENTION

1. Technical Background

The present invention relates to a medical filter which can be placed inside a blood vessel or other body passage for the purpose of intercepting thrombus or particles, which may be optionally retrieved at a later time.

2. Discussion

Some basic types of medical filters are generally known, wherein a single filter element, mesh or member extends across the direction of flow inside a blood vessel. Several features are desirable for medical filters, including non-surgical or percutaneous delivery of the filter to a desired site, and expansion from a preferably small initial size to an expanded working size that matches the vascular anatomy at the desired site. Also, a medical filter should of course preferably capture a sufficient percentage of thrombus, while allowing blood to flow freely through the filter.

Another desirable feature is a capability to remain in the desired position for treatment through a period of time, and also to offer the physician the option during that time of leaving the filter in place permanently, or retrieving the filter when no longer needed.

In addition, a medical filter should preferably have a design whereby the filter is stable in the vessel, such that the filter has little or no tendency to "tilt" and may become less effective in capturing thrombus. Some medical filters may be used in the vena cava, and may be described in such event as a "vena cava filter."

Prior medical filters may consist of a network of interconnected ribs, which extend substantially in a radial direction in relation to the blood vessel. Unfortunately, an entire filter may shift position if one of the ribs were to break. In addition, the free ends of the ribs, which may be positioned under a certain pressure against the internal wall of the blood vessel, may cause trauma to the vessel wall, or may become embedded within.

Another possible design is essentially a screen placed across a transverse dimension of a vessel. Again, it is important to take measures to resist "tilting" by this screen type of filter.

A disadvantage of some known medical filters may be a possibility of shifting position or tilting inside the blood vessel, even when the filter maintains its proper shape, if a prior filter may have been incorrectly placed in a blood vessel which is too wide. In such an event, a medical filter may not grab sufficient hold on the internal wall of the blood vessel.

A medical filter may be delivered through a catheter in a compressed shape, where it tends to resiliently expand within the blood vessel. The medical filter may tend to trap thrombus or particles, and resist their movement further downstream. The filter may include, in a position of use, an outer shape corresponding to the internal diameter of the blood vessel transverse to the longitudinal direction hereof.

A medical filter which may also be implanted permanently or temporarily. It is preferable to implant the filter initially without deciding at that time whether the filter will eventually be retrieved or is to remain permanently. It is also desirable that if the filter is retrieved, then it should be retrieved as easily as possible.

To help in successful retrieval, a desirable factor is to avoid endothelialization or in-growth of the vessel wall around the structural members of the filter.

On a retrievable filter, it is also desirable to provide releasable temporary position stabilizers, to resist a possibility of tilting and to enhance position retention.

Some medical filters provide anchors or small barbs, which extend at various angles in radial directions outward from the ribs. One successful design which is sufficient for a variety of applications is shown in the commonly owned U.S. Pat. No. 6,443,972, entitled "Vascular Filter" which issued to at least one of the co-inventors of the present invention on Sep. 3, 2002. This patent shows many desirable features for filters, including a longitudinally stable central body section, and two filter sections providing multiple filtering action. Other advantageous features are that it is preferably made of a single piece of resilient material, and can be implanted through a catheter without requiring surgery.

A filter may be provided with barbs or anchors for increasing position retention. The barbs tend to gently hold the filter in place inside the blood vessel, and so it is of course desirable to avoid endothelialization of the filter components, to facilitate its retrieval.

Also, medical filters of the present invention that are retrievable, rather than permanent filters, may provide an additional advantage. When a medical filter is retrieved from a blood vessel, the entire filter is resiliently compressed to a relatively small diameter, for extraction through a catheter.

The filter may preferably have a hook structure at one or both ends, of a design that preferably provides multiple hook surfaces for increasing ease of retrieval.

A filter according to the present invention may also preferably have one or more small barbs or anchors. An additional design is to provide a filter with a hook structure at one end, and cooperating barbs for holding the filter in position, that are arranged to pull out gently if the filter is retrieved in a retrieval direction by pulling on the hook structure with a retrieval snare or other retrieval device.

With a medical filter according to the present invention, a tubular section may tend to resiliently exert slight pressure along a large section of contact area on the wall of the blood vessel or other body passage, which tends to hold itself in place. The medical filter will consequently tend not to shift position.

The term "tubular" is used in its broadest sense, to encompass any structure arranged at a radial distance around a longitudinal axis. Accordingly, tubular includes any structure that (i) is cylindrical or not, such as for example an elliptical or polygonal cross-section, or any other regular or irregular cross-section; (ii) has a different or changing cross-section along its length; (iii) is arranged around a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; (vi) has any desired combination of length or cross-sectional size.

In addition, the medical filter according to the present invention tends not to rotate transversely or tilt over, which is another advantage of the present invention. In a possible embodiment, a medical filter according to the present invention may preferably be formed out of one single piece, which provides advantages including simplicity of manufacture.

In a preferred embodiment, a medical filter according to the present invention includes a first and second filter section, arranged on either side of a central body section. The body section and the filter sections thus enclose a space. Due to the elongated shape of the medical filter according to the present invention, and the arranging of the first and second section on either side of the body member, the present filter has an enhanced filtering effect. In other words, two filtering structures have been created for intercepting thrombus, particulates or other matter moving inside the blood vessel or other body passage.

Another possible embodiment of the filter according to the present invention is that, when seen in an axial or longitudinal direction, the filter sections have the shape of a regular polygon, and provide several smaller filtering "cells." The purpose of these filtering cells is to intercept thrombus moving inside a blood vessel, and the smaller filtering cells tend to capture more thrombus.

The filter sections, as arranged according to an embodiment described above on either side of the tubular body section, may be identical in shape, thereby enhancing the simplicity of the medical filter according to the present invention.

Another possible benefit of the present invention relates to endothelialization, which is the healing of the vessel inner surface by endothelial cells. It is desirable not to damage these endothelial cells when removing a retrievable medical filter, and the improved designs of the present invention tend to minimize any impact during retrieval.

Some medical filters may have been made of a braiding of wire-like elements, or a tubular element also having a series of cuts at places corresponding to the positions of passages. It is thus possible to build various medical filters according to the present invention, by various techniques and of various materials to obtain the ultimate shape and desired design. Possible junctions of filter components may be formed by melting or welding free ends together, or by employing such a cutting pattern that the basic shape of the medical filter according to the present invention is obtained.

It should be noted that the present invention also relates to methods for using implantable filters as described herein.

These and various other objects, advantages and features of the invention will become apparent from the following description and claims, when considered in conjunction with the appended drawings. The invention will be explained in greater detail below with reference to the attached drawings of a number of examples of embodiments of the present invention.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

A medical filter according to the present invention is illustrated in FIGS. 1–8. The filter 10 is preferably made of a resilient material, and tends to expand from an initial compressed shape to an expanded shape, as depicted diagrammatically in FIG. 9.

Figure 1:
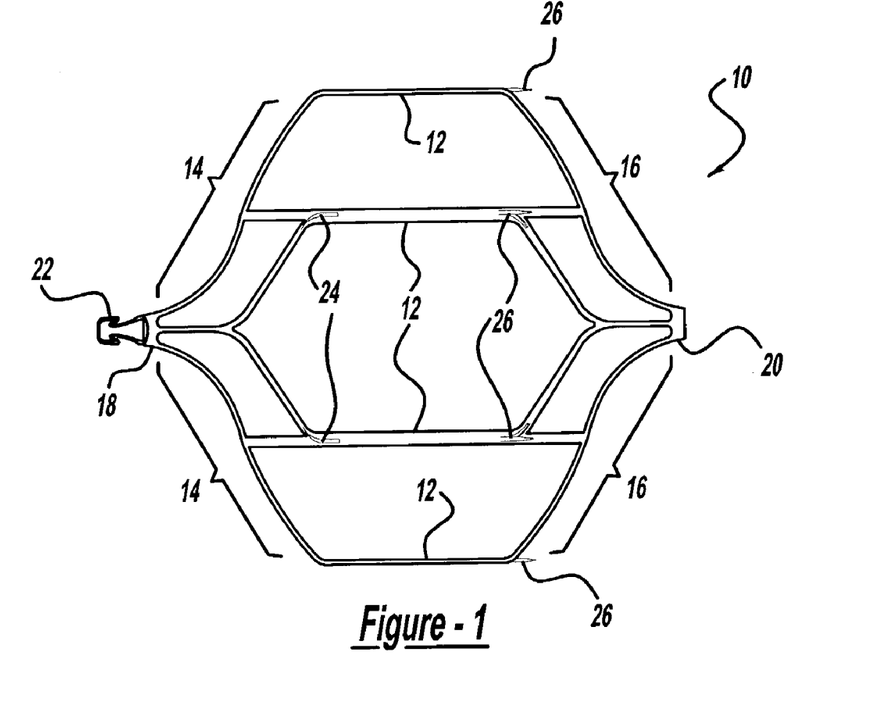
FIG. 1 shows a side elevation view of a filter arranged according to the principles of the present invention, in an expanded shape.
Figure 2:
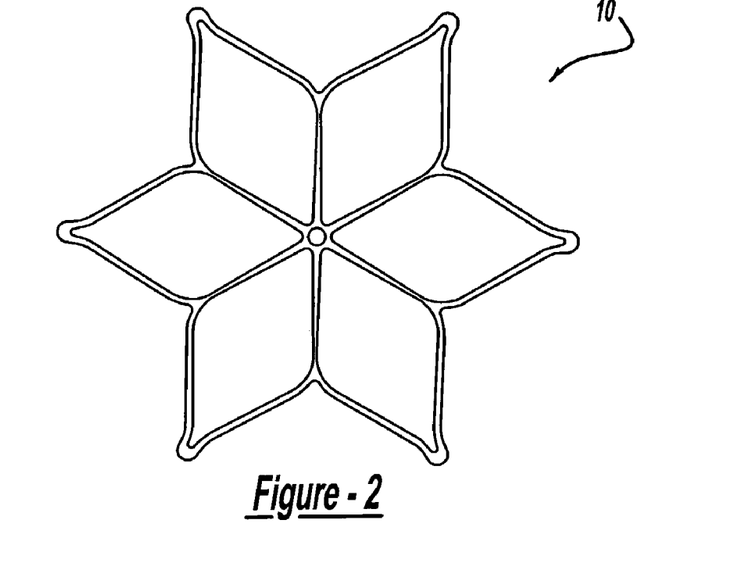
FIG. 2 illustrates an end elevational view along a longitudinal axis of a filter according to the principles of the present invention, in an expanded configuration.

In the expanded shape, the filter 10 preferably has a series of longitudinal ribs 12, aligned essentially parallel with a longitudinal axis of the filter 10. A plurality of members preferably define a first and second filter section 14 and 16, arranged near a retrieval end of the filter and an insertion end, respectively. A pair of central collars 18 and 20 are also preferably positioned at the retrieval end and the insertion end, respectively. A hook structure 22 is attached to the retrieval collar 18.

In addition, a series of apertures 24 and a corresponding series of anchoring barbs 26 are preferably positioned at shoulders or transitions between a central body section 15 defined by the longitudinal ribs 12 and the filter sections 14 and 16, respectively. In other words, the apertures 24 are located between the ribs 12 and the filter section 14 at the retrieval end, and the barbs 26 are located between the ribs 12 and the filter section 16 at the insertion end of the filter 10.

Figure 10:
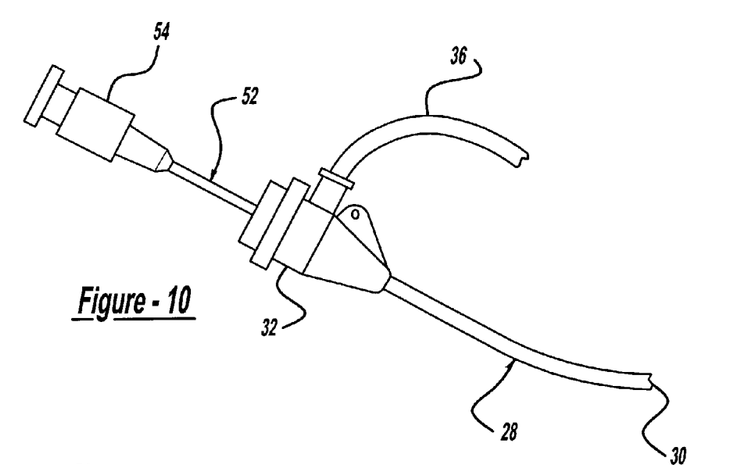
FIGS. 10–11 and 20–22 show accessory devices that may be used to deliver implantable filters of the present invention.
Figure 11:
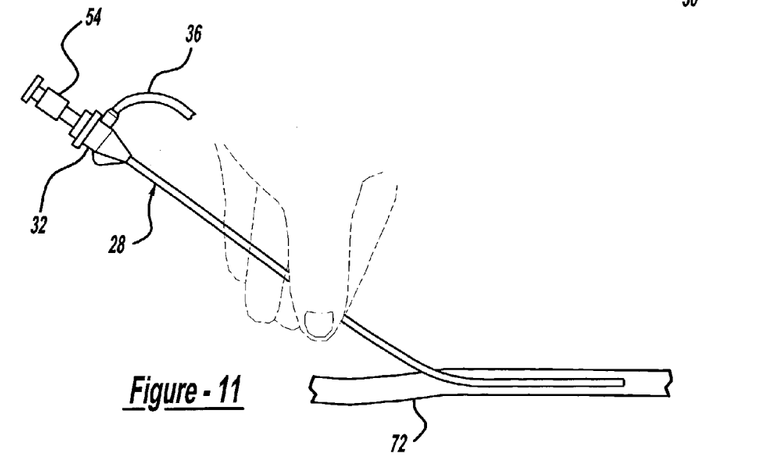

The filter 10 is preferably delivered to a desired site for treatment by a delivery catheter 28, which preferably defines a lumen 30 extending between a proximal hub 32 having a hemostatic valve (not shown) and a distal lumen opening 34. The proximal hub 32 also preferably has a flush lumen tube 36 and a stopcock 38, which may be used for various therapeutic purposes, including flushing the lumen 30 of the delivery catheter 28, injecting radiopaque contrast fluid for viewing on an x-ray video screen, or delivering medications.

Figure 12:
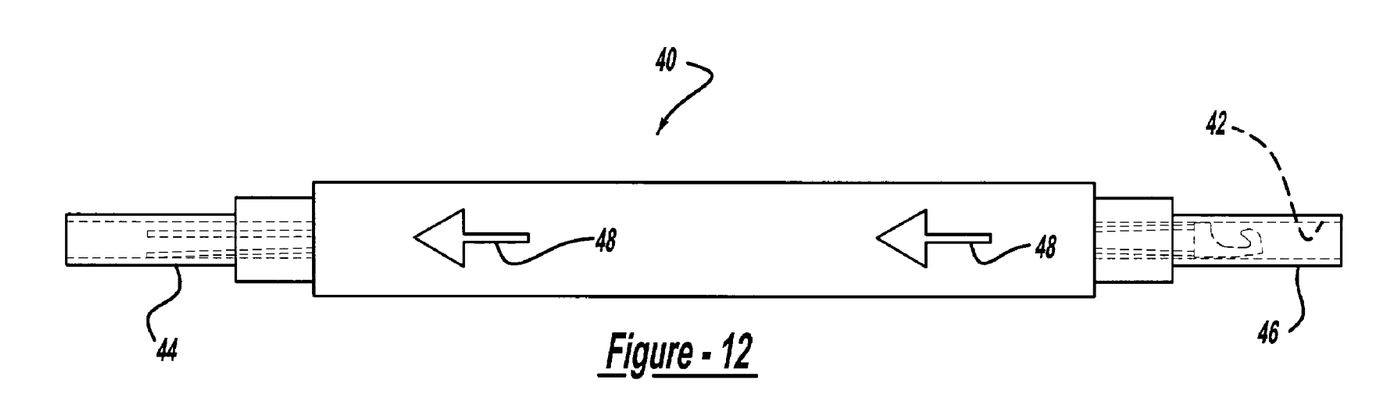
FIGS. 12–13 show side elevational views of a storage and insertion cartridge for a medical filter.
Figure 13:
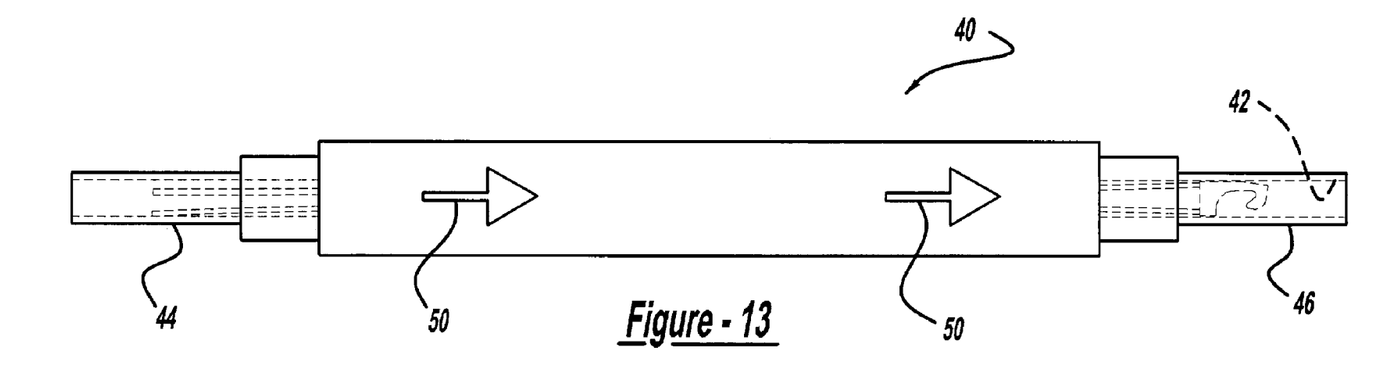
Figure 24:
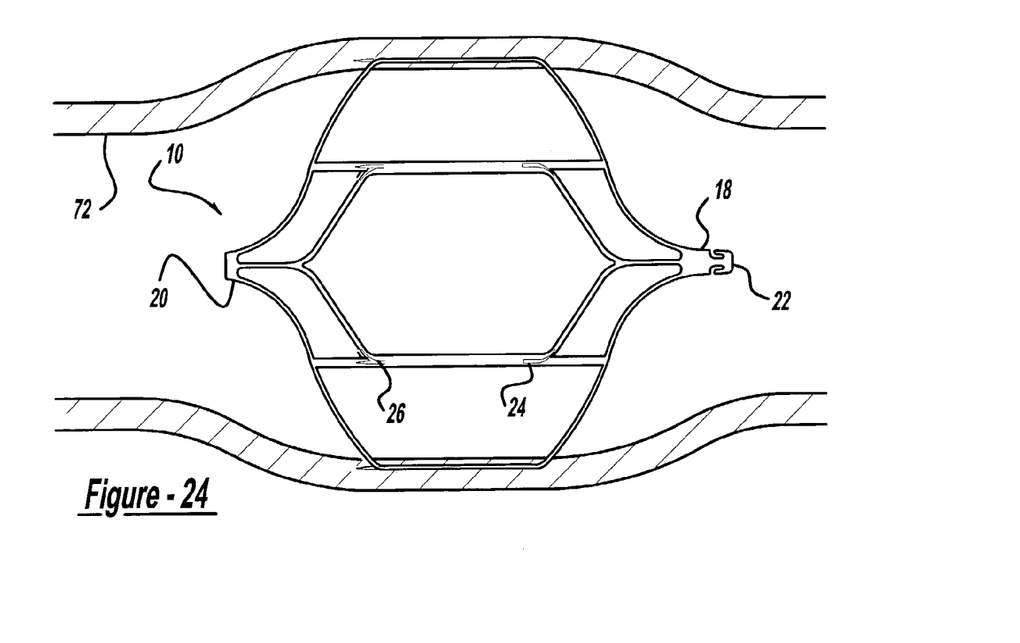

The filter 10 is preferably initially packaged in a compressed state in a filter cartridge 40, shown in FIGS. 12 and 13. The cartridge 40 defines a lumen 42, in which the compressed filter is stored. If the filter 10 is to be used in a blood vessel, the physician should preferably be able to easily determine which end of the cartridge 40, and thus which end of the filter 10, should be inserted first. The filter 10 can accordingly be correctly arranged in the body passage or blood vessel 72, as shown in FIG. 24. The cartridge 40 shown in FIGS. 12 and 14 also preferably has a femoral jack 44 and a jugular jack 46, which preferably have different shapes, to correspond with matching femoral and jugular access delivery catheter systems, respectively. Such different shapes may for example include, when viewed from an end of the cartridge 40, a circle, a square or a triangle. The cartridge also preferably has femoral arrows 48 with a label (not shown) indicating that the femoral jack 44 is to be used for inserting the filter 10 from a femoral access direction, as well as jugular arrows 50 with a label (not shown) indicating that the jugular jack 46 is to be used for inserting the filter 10 from a jugular access direction.

Figure 3:
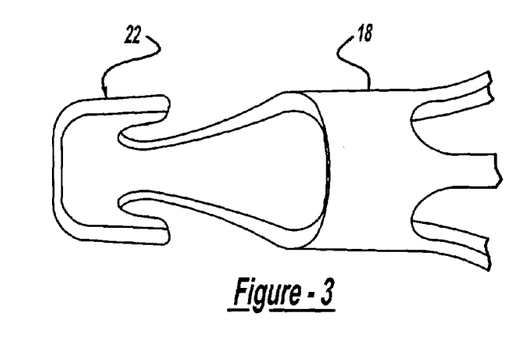
FIGS. 3 and 4 show partial elevation views of a hook structure of a filter according to the principles of the present invention.
Figure 4:
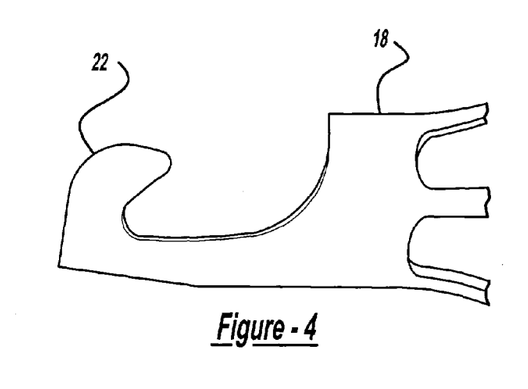

The hook structure 22 of filter 10 may have a T-shape, as shown in FIGS. 3 and 4, with twin hooks. It is possible that this twin hook structure 22 may improve the ease of retrieving the filter 10.

Figure 5:
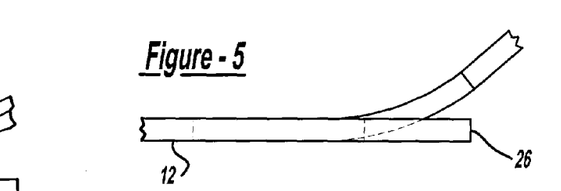
FIGS. 5–8 show partial views of shoulder portions of a medical filter, according to the principles of an embodiment of the present invention.
Figure 6:
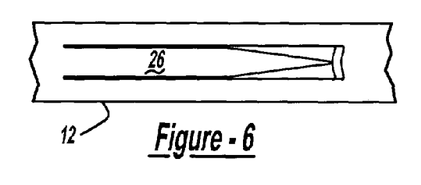
Figure 7:
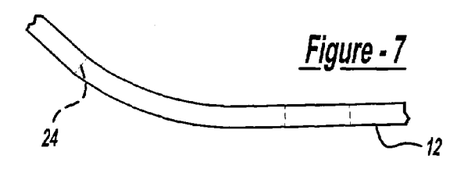
Figure 8:
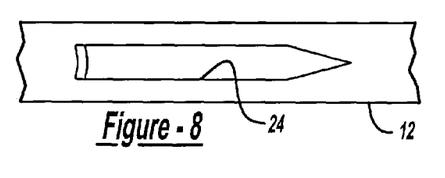
Figure 9:
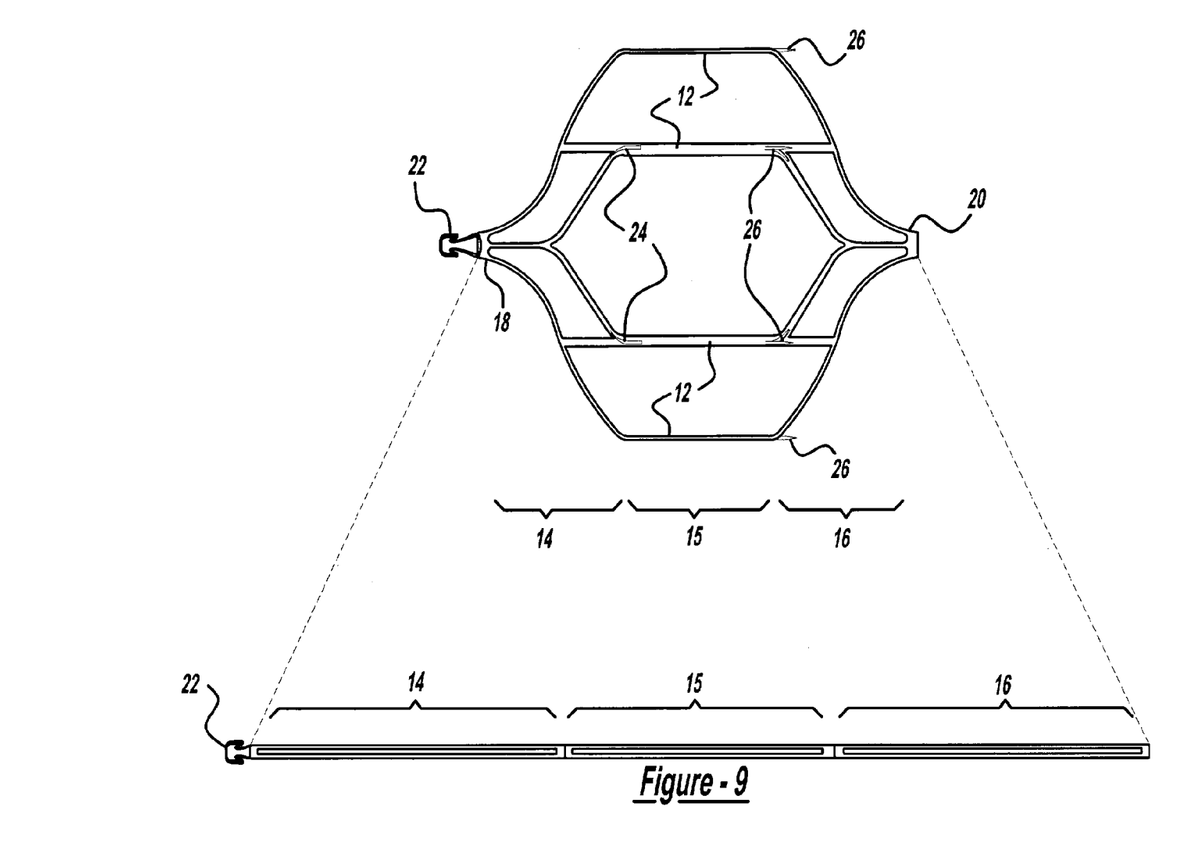
FIG. 9 is a diagrammatic view of a filter in an initial compressed shape and an expanded deployed shape.

The barbs or anchors 26 extend in a longitudinal direction, and are exposed when the filter 10 is in an expanded shape. As shown in FIGS. 1, 5 and 9, the anchors 26 and the second filter section 16 define an acute angle. They may be formed as shown in FIGS. 5 and 6, in which a series of cuts in the ribs 12 both shape the anchor 26 and define an aperture for the anchor 26 when the filter is in a compressed shape.

The apertures 24 may tend to balance stresses in the filter. In other words, anchors 26 may be formed by cutting them out of the ribs, which will tend to bend and define the center section 15 and the filter section 16. Similarly, the presence of apertures 24 may tend to balance stresses in the ribs, causing them to bend in a complementary manner and define the center section 15 and the filter section 14.

In use, delivery catheter 28 is inserted along a body passage in a patient until distal end 34 is near a desired site for treatment. After filter 10 is disposed within lumen 30 of catheter 28, a push wire 52 may be used to eject the filter 10 from the distal tip 34 of the catheter 28. Push wire 52 shown in FIGS. 10 and 11 has a proximal hub 54. and a distal end 56. Filter 10 is introduced into the body passage, where the medical filter 10 will resiliently expand after being released from the catheter 28, under the influence of expansive forces inherent to the material of which the medical filter has been made, into the illustrated shape.

Of course, several methods are possible for placing the filter inside lumen 30 of the catheter 28. The filter may simply be placed inside the lumen 30 distal end 34, providing a relatively short distance the filter 10 must be pushed before exiting the catheter 28.

Another possible method for inserting filter 10 at the desired site is to insert it into the lumen 30 proximal end, and then push the filter 10 with a push wire 52 along the entire length of the catheter 28, after the catheter, after the catheter distal end has been advanced to the desired position for treatment.

Another possible aspect is to provide positive feedback on which the end of the filter 10 is inserted first into lumen 30. In other words, it may be desirable to insert one end of the filter into the catheter first, for example when approaching from a femoral access point, and the other end of the first being inserted first at a different access point, for example when approaching a jugular access point. The cartridge 40 shown in FIGS. 12 and 13 may facilitate arranging the filter 10, including a first series of arrows 48 having a first label or indicator such as "Femoral", and a second series of arrows 50 having a second label or indicator such as "Jugular".

Figure 14:
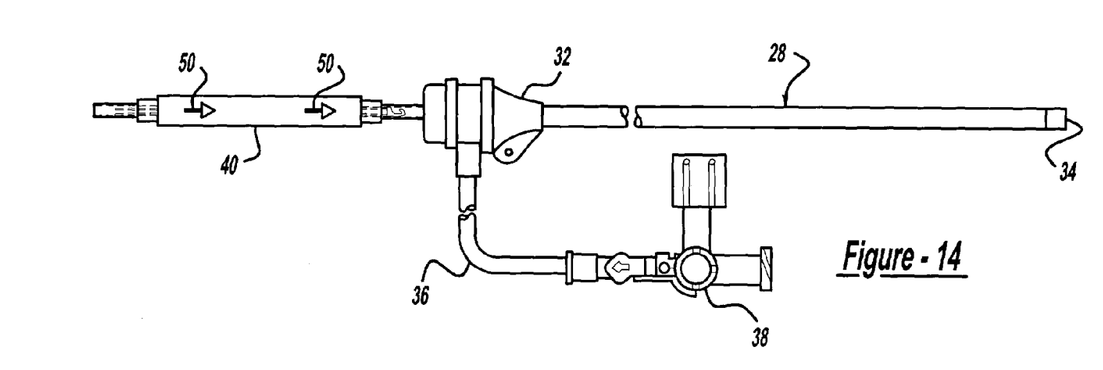
FIGS. 14–19 show diagrammatic views of methods for delivering and deploying a filter of the present invention.
Figure 15:
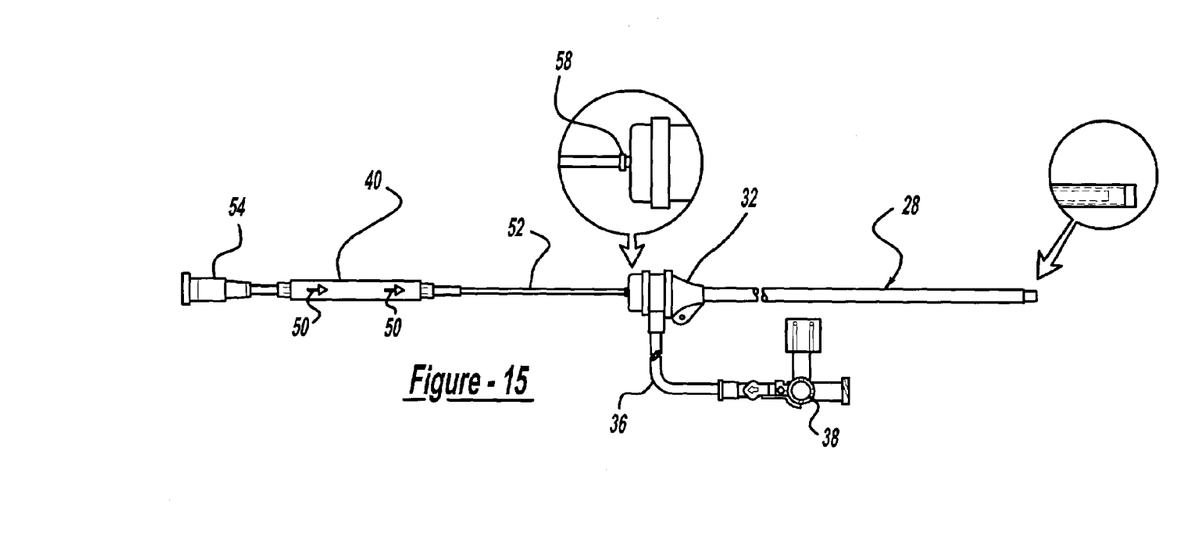
Figure 16:
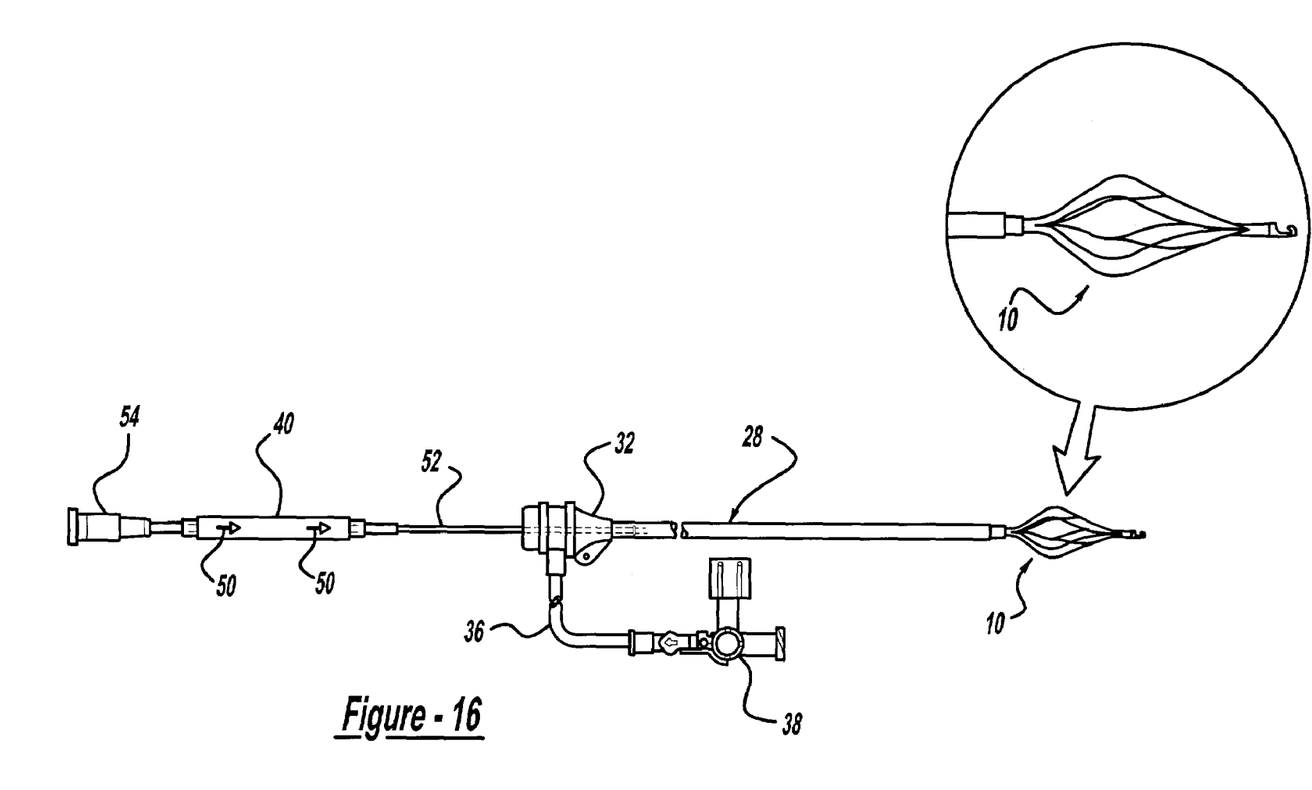

For example, with reference to FIGS. 14–16, if a jugular approach is selected by the physician (or any other access point where it is desirable that the filter 10 be inserted with to hook structure 22 lead in first), the physician may refer to the "Jugular" arrows 50 and insert the corresponding jugular jack 46 at one end of the cartridge 40 into the proximal hub and hemostatic valve 32 of the catheter 28. Next, push wire 52 is advanced into to other end of the cartridge 40, and through to lumens of the cartridge 40 and to catheter 28 until a marker 58 reaches the hemostatic valve, This marker 58 may be provided at a position such that to push wire distal end will have positioned the filter 10 to a point where it has reached the distal end of the catheter 28. At this arrangement, the physician may re-position the assembly to refine the location of the filter 10 just before deploying the filter.

Figure 17:
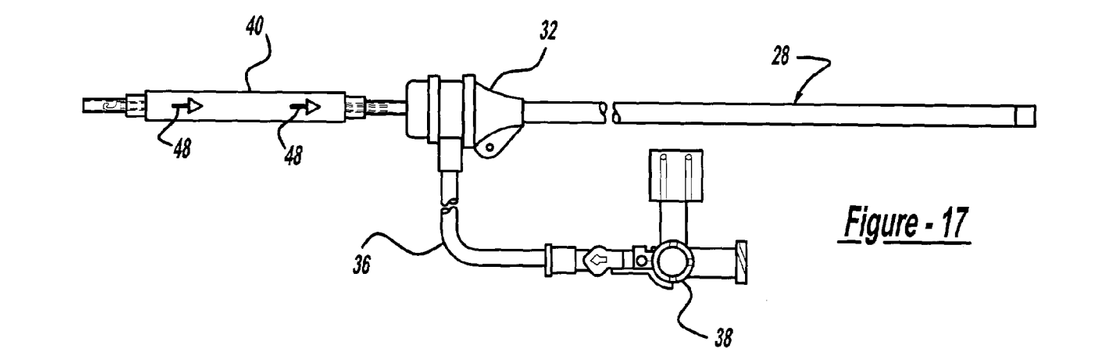
Figure 18:
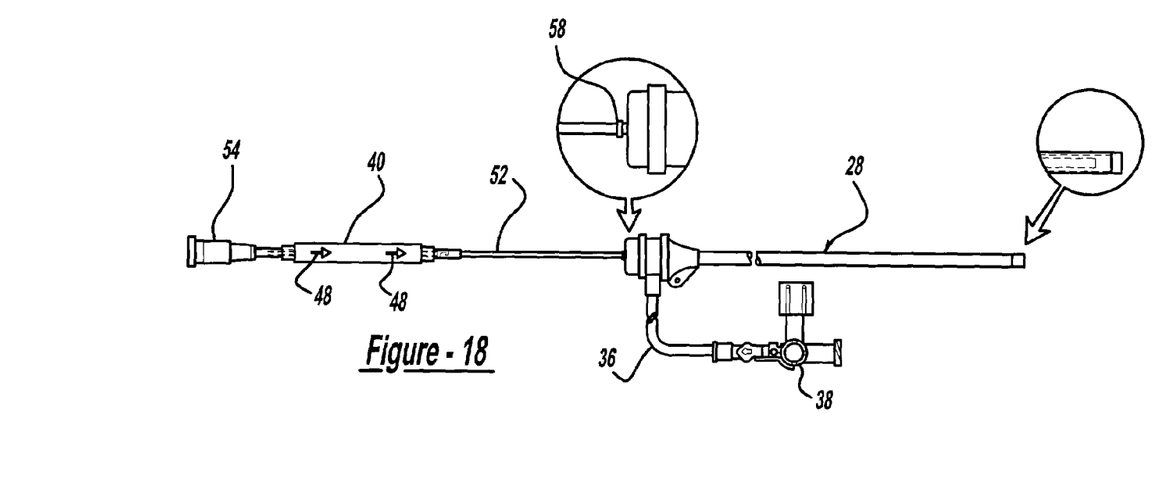
Figure 19:
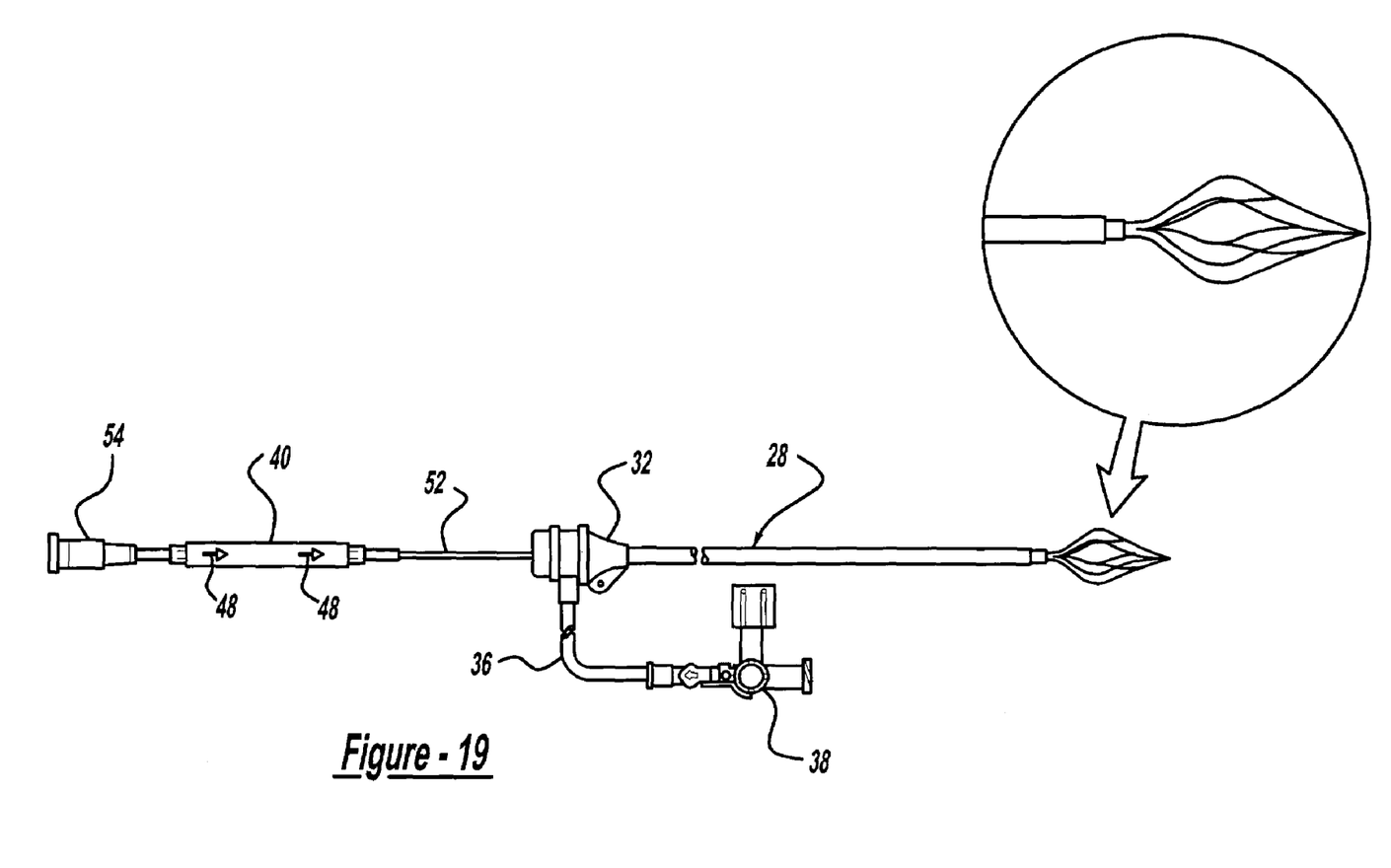

As another example, the physician may choose a femoral access point (or any other access point where the physician desires to insert the filter 10 with the collar 20 end first). In this kind of situation, the physician may choose a catheter 28 having a length suitable for such desired site for treatment, as shown in FIGS. 17-19.

Accordingly, the physician would in such a case refer to the "Femoral" arrows 48, and insert the corresponding femoral jack 44 on the cartridge 40 into the proximal hub 32. The push wire 52 is used to advance and deploy the filter 10 as described above.

Figure 20:
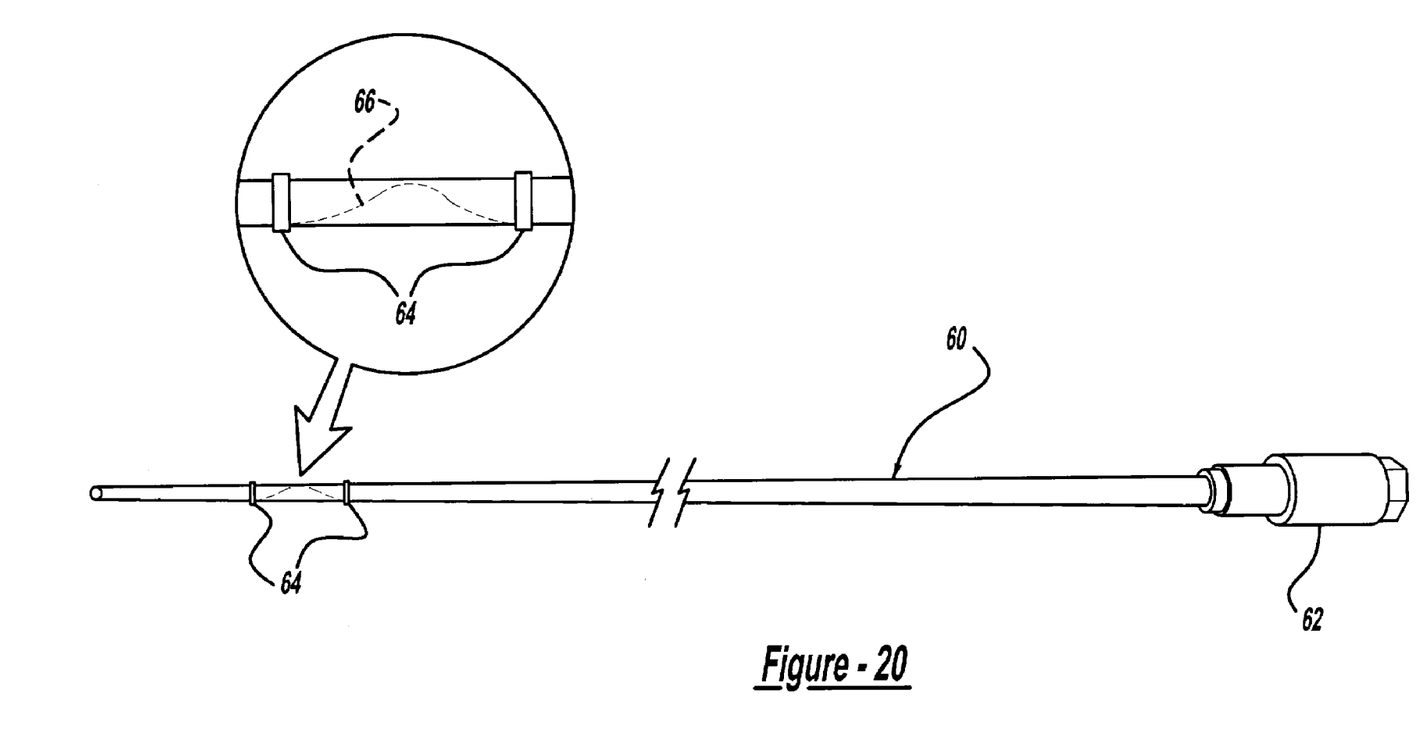
Figure 21:
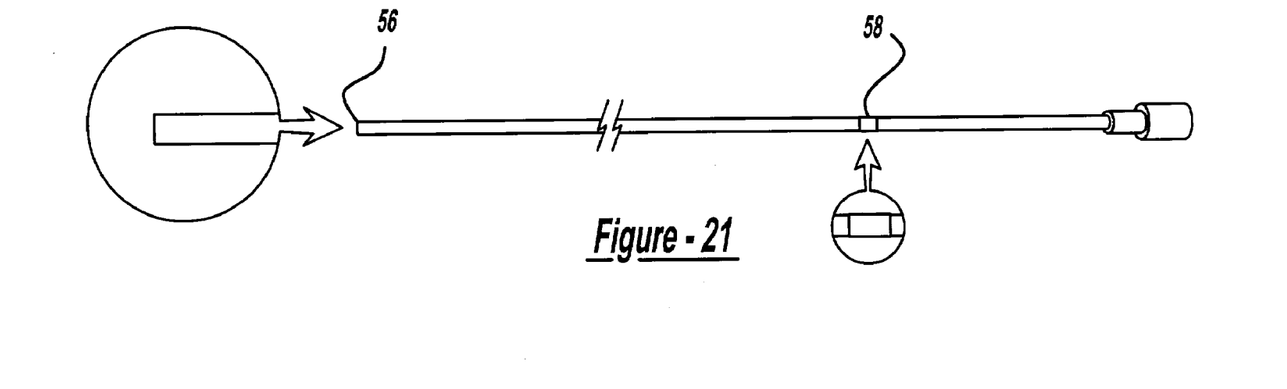
Figure 22:
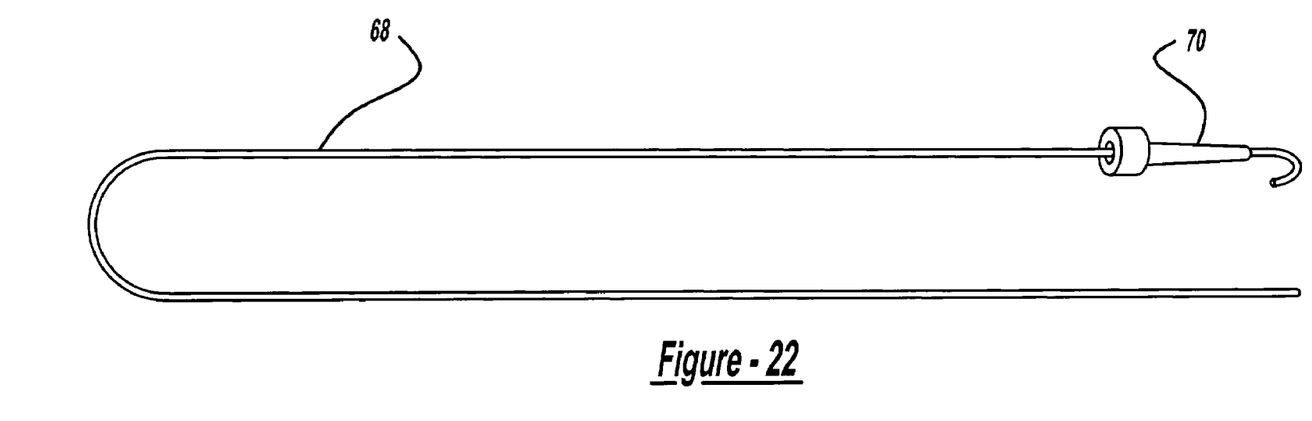
Figure 23:
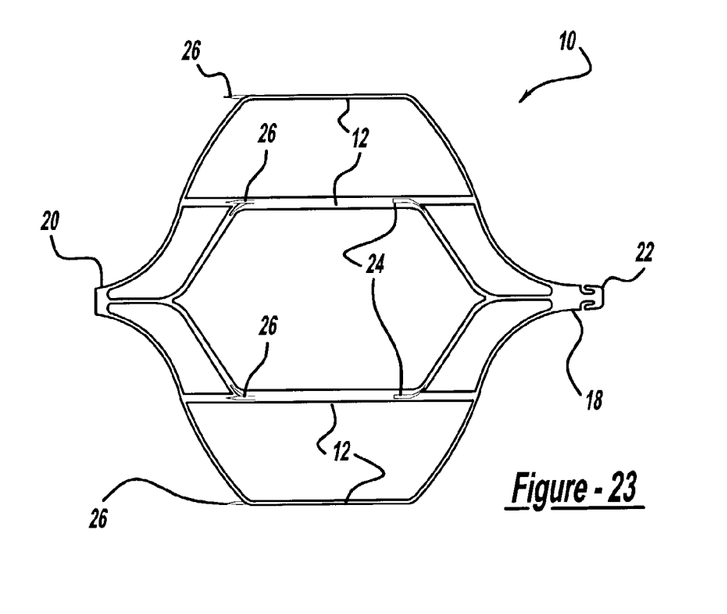
FIGS. 23–24 show cross-sectional views of a medical filter according to the present invention, alone and implanted in a body passage of a patient.

Optional devices that may be used, in particular for example before the catheter 28 is inserted and advanced to the desired site for treatment, are a guidewire 68 and a complementary introducer 70 as shown in FIG. 22. The dilator 60 shown in FIG. 20 has a proximal hub 62 and spiral sideholes 66, flanked by markers 64. Another optional device that may be used, in particular when the catheter 28 is inserted and advanced to the desired site for treatment, is a dilator 60. The dilator 60 shown in FIG. 20 has a proximal hub 62 and spiral sideholes 66, flanked by markers 64.

Medical filters according to the present invention may be made of any suitable material using a variety of methods. One material having the desired characteristics of strength, resilience, flexibility, biocompatibility and endurance is nitinol. Other materials having the desired characteristics may be used, such as stainless steel. Likewise, the manufacturing methods may include providing a tube, and then cutting a pattern into the tube to enable expansion into the desired shape. Various other methods are of course possible, including forming the filter of discrete members and then joining or connecting the members.

In addition to the nitinol mentioned so far, many other materials may also be used for manufacturing a medical filter according to the present invention. By way of alternative, various metals may for instance be used, in which case it is essential that the medical filter assumes the intended shape hereof after having been ejected from the catheter for the purpose of introduction hereof. The medical filter, during introduction, is of course kept in a compressed state, by the catheter. To this end, a configuration may be used decompressing the filter metal due to the elastic properties hereof.

In the axial view, the filter sections on either side of the ribs of the medical filters according to the present invention described above display diamond or polygon shapes. It is also possible to suffice with medical filters of which the filter sections display in axial view a star shape, or any other suitable shape, as long as they intercept blood clots or thrombus successfully. An advantage of this feature is that, after passing the first filter section and the tubular section or the elongated body member, a second chance at interception in the form of an additional filter section has been provided. Also, other shapes of the filter sections in axial view are possible, which shapes will occur to those skilled in the field after reading the present description. The shapes of the filter sections in axial view need not be symmetrical, and may have in principle any suitable appearance.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A medical filter for placement inside a body passage to treat a patient, comprising:

in a radially compressed state, a tubular shape having a first and second integral end piece at a first and second end of the medical filter; a plurality of ribs arranged in a preselected pattern and extending between the first and second end piece in a direction substantially parallel to a longitudinal axis of the medical filter; the pattern of ribs defining a central body section and a first and second end section; a hook structure affixed to the first end piece; at least one barb pattern defined at a transition between at least one rib of the central body section and the second end section; and at least one aperture defined at a transition between at least one rib of the central body section and the first end section;

in a radially expanded deployed state, the ribs tend to resiliently expand in radial directions, thereby causing the first and second end pieces to move toward each other; each of the ribs tending to spread apart, such that the medical filter defines a plurality of central polygon shapes arranged adjacently around a longitudinal axis of the medical filter, each of the ribs defining each polygon shape contending in a plane substantially parallel to the longitudinal axis of the medical filter; the medical filter further defining a first and second end filter portion connecting the central polygons with the end pieces, wherein the end filter portions each define a plurality of filter cells; each of the filter cells being formed by a plurality of members; the filter cells all extending along a first and second end cone;

the at least one barb pattern defining at least one anchor extending substantially parallel to the longitudinal axis, defining an acute angle between the barb and the second end cone in the expanded deployed state, which tends to resist movement of the filter in a body passage;

wherein the medical filter may be implanted in a body passage for a period of time, and the medical filter may optionally be retrieved by pulling on the hook structure and withdrawing the filter out of a patient through a catheter;

the at least one barb extending away from the hook structure, such that the filter is more easily retrievable.

2. The medical filter as set forth in claim 1, wherein the filter is formed of one single unitary metal element.

3. The medical filter as set forth in claim 1, adapted for use in the vena cava.

4. The medical filter as set forth in claim 1, wherein each rib has one of the barbs, and each rib defines one of the apertures; the apertures cooperating with the barbs to balance structural stress over the first and second ends of the filter.

5. The medical filter as act forth in claim 1, wherein the hook structure has more than one retrieval surface.

6. The medical filter as set forth in claim 1, wherein the book structure has two or more hooks, arranged at an angle to each other.

7. The medical filter as set forth in claim 1, wherein the hook structure has a central portion that is bent radially inward toward the longitudinal center axis of the filter.

* * * * *